US011490618B2

(12) United States Patent
Campbell-Lee et al.

(10) Patent No.: US 11,490,618 B2
(45) Date of Patent: Nov. 8, 2022

(54) PRESERVATION COMPOSITIONS

(71) Applicant: Conopco, Inc., Englewood Cliffs, NJ (US)

(72) Inventors: Stuart Campbell-Lee, Wirral (GB); Rupak Mitra, Bangalore (IN); Thomas Richard Pointon, Warrington (GB); Ian Peter Stott, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 17/056,472

(22) PCT Filed: May 20, 2019

(86) PCT No.: PCT/EP2019/062962
§ 371 (c)(1),
(2) Date: Nov. 18, 2020

(87) PCT Pub. No.: WO2019/233752
PCT Pub. Date: Dec. 12, 2019

(65) Prior Publication Data
US 2021/0307324 A1 Oct. 7, 2021

(30) Foreign Application Priority Data
Jun. 4, 2018 (EP) .................................... 18175856

(51) Int. Cl.
| | | |
|---|---|---|
| *A01N 37/06* | (2006.01) | |
| *A01N 25/02* | (2006.01) | |
| *A01N 31/06* | (2006.01) | |
| *A61K 8/00* | (2006.01) | |
| *A61Q 5/00* | (2006.01) | |
| *A61K 8/34* | (2006.01) | |
| *A61K 8/362* | (2006.01) | |
| *A61Q 19/00* | (2006.01) | |

(52) U.S. Cl.
CPC .............. *A01N 37/06* (2013.01); *A01N 25/02* (2013.01); *A01N 31/06* (2013.01); *A61K 8/00* (2013.01); *A61Q 5/00* (2013.01); *A61K 2800/524* (2013.01)

(58) Field of Classification Search
CPC ........ A01N 37/06; A01N 25/02; A01N 31/06; A61K 8/00; A61K 2800/524; A61K 2800/10; A61K 8/34; A61K 8/342; A61K 8/362; A61Q 19/00; A61Q 5/00
See application file for complete search history.

(56) References Cited

U.S. PATENT DOCUMENTS

| | | |
|---|---|---|
| 3,448,132 A | 6/1969 | Griebstein |
| 5,580,849 A | 12/1996 | Dyet et al. |
| 7,074,747 B1 | 11/2006 | Lukenbach et al. |
| 9,326,924 B1 | 5/2016 | Fourre et al. |
| 2008/0063618 A1 | 3/2008 | Johnson et al. |
| 2012/0101135 A1 | 4/2012 | Klug |
| 2012/0329874 A1 | 12/2012 | Piva et al. |
| 2014/0311515 A1 | 10/2014 | Barne et al. |
| 2016/0000094 A1 | 1/2016 | Modak et al. |
| 2016/0060660 A1 | 3/2016 | Hiller et al. |
| 2017/0151165 A1 | 6/2017 | Scheunemann et al. |
| 2017/0360663 A1 | 12/2017 | Schulze Zur Wiesche et al. |

FOREIGN PATENT DOCUMENTS

| | | |
|---|---|---|
| BR | 102017003313 | 10/2018 |
| CN | 1366874 | 9/2002 |
| CN | 103998011 | 8/2014 |
| CN | 104078093 | 10/2014 |
| CN | 104152300 | 11/2014 |
| CN | 105133035 | 12/2015 |
| CN | 105296995 | 2/2016 |
| CN | 105457059 | 4/2016 |
| CN | 104116734 | 5/2016 |
| CN | 106565986 | 4/2017 |
| CN | 107189771 | 9/2017 |
| CN | 107519516 | 12/2017 |
| CN | 107937150 | 4/2018 |
| DE | 102017101868 | 9/2017 |
| DE | 202017001430 | 9/2017 |
| EP | 0853941 | 7/1998 |
| EP | 1082906 | 3/2001 |
| EP | 1433464 | 6/2004 |
| EP | 2807925 | 12/2014 |
| EP | 2320860 | 10/2017 |
| FR | 2877576 | 5/2006 |
| JP | 2001226205 | 8/2001 |
| JP | 2010239872 | 10/2010 |
| JP | 2018048104 | 3/2018 |
| WO | WO9405758 | 3/1994 |
| WO | WO9849257 | 11/1998 |
| WO | WO0061107 | 10/2000 |
| WO | WO2007084607 | 7/2007 |
| WO | WO2009019255 | 2/2009 |
| WO | WO2010018385 | 2/2010 |
| WO | WO2011092325 | 8/2011 |
| WO | WO2012135282 | 10/2012 |
| WO | WO2014161988 | 10/2014 |
| WO | WO2015197377 | 12/2015 |
| WO | WO2018092075 | 5/2018 |

OTHER PUBLICATIONS

Search Report and Written Opinion in EP18175825; dated Aug. 22, 2018; European Patent Office (EPO).
Liquid Detergent for Sensitive Skin; Liquid Detergent; Nov. 1, 2015; pp. 1-3.
Fortifying Shampoo; Fortifying Shampoo; Apr. 1, 2018; pp. 1-2.
Search report and Written Opinion in EP18175793; dated Jan. 8, 2019.
GNPD MINTEL; GNPD Mintel; Shampoo Sunsilk Deeply; Jan. 2009; pp. 1-2 (also as XP002786946).
Advanced Repairing Shampoo; Database GNPD Mintel; 2018; pp. 1-2 (also as XP002786947).

(Continued)

*Primary Examiner* — Trevor Love
(74) *Attorney, Agent, or Firm* — Foley & Lardner LLP

(57) ABSTRACT

A preservation system comprising: i) itaconic acid or salt thereof and ii) a secondary preservation chemical selected from the list consisting of terpineol, geraniol, perillyl alcohol, menthol, terpinene, linalool, citronellol and mixtures thereof.

13 Claims, No Drawings

(56) References Cited

OTHER PUBLICATIONS

Search Report and Written Opinion in EP18209553; dated May 21, 2019.
Search Report and Written Opinion in EP18209554; dated May 21, 2019.
Search Report and Written Opinion in PCTEP2019062973; dated Jun. 25, 2019.
Search Report and Written Opinion in PCTEP2019062963; dated Jul. 5, 2019.
Search Report and Written Opinion in PCTEP2019062983; dated Jul. 8, 2019.
Search Report and Written Opinion in PCTEP2019062974; dated Jul. 8, 2019.
Search Report and Writtion Nopinion for PCTEP2019062962; dated Aug. 2, 2019.
Search Report and Written Opinion in EP19189592; dated Oct. 18, 2019.
Somayeh Ghahari ; Phytochemical screening and antimicrobial activities of the constituents isolated from Koelreuteria paniculata leaves; XP55625821 Natural Product Research; Oct. 2, 2015; pp. 1865-1869; vol. 29, No. 19.
NYKAAFRONTENDTEAM; Dhathri Dheedhi Anti-Dandruff for removing dandruff naturally herbal shampoo; XP055626744 URL:https://www.nykaa.com/dhathri-dheedhi-anti-dandruff-for-removing-dandruff-naturally-herbal-shampoo-100ml/p/417720; Jun. 18, 2019; whole document.
Pan Chun-Xiu ; Investigation on the Macromolucuilar Network Structure of Xianfeng Lignite by a New Two-Step Depolymerisation; Fuel, IPC Science & Technology Press; Dec. 8, 2012; pp. 49-53; vol. 109.
Search Report and Written Opinion in EP19189595; dated Oct. 18, 2019.
Luan Harding H et al; Food Fight : Role of Itaconate and Other Metabolites in Antimicrobial Defense; Sep. 13, 2016; pp. 379-387; vol. 24 No. 3.
Search Report and Written Opinion in PCT EP2019 081382; dated Jan. 21, 2020.
Partial Search Report and Provisional Written Opinion in PCTEP2019081362; dated Jan. 21, 2020.
Search Report and Written Opinion in PCTEP2019081362; dated Mar. 16, 2020.
Search Report and Written Opinion inPCTEP2020070904; dated Oct. 20, 2020.
IPRP2 in PCTEP2020070905.; Jul. 8, 2021.
Rybicki et al,; Molecular tracers preserved in Lower Jurassic "Blanowice brown coals" from southern POland at the onset of colaification: Organic geochemical and petrological characteristcs; Organic Geochemistry; 2016; pp. 77-92; 102.
4-Oxovaleric acid,; Surfactant.top; Aug. 26, 2021; pp. 1-4, https://www.surfactant.top/en/saa/?type=detail&id=7524.
Anti-Dandruff (Coal Tar) Topical: Uses, Side Effects, Interactions, Pictures, Warnings and Dosing WebMD; 2017; pp. 1-4 (URL:https://web. archive,org/web/20170802013524/https:/).
Search Report and Written Opinion in EP18175856; dated Jul. 6, 2018; European Patent Office (EPO).
Search Report and Written Opinion in EP18175850; dated Jan. 3, 2019; European Patent Office (EPO).
Color-Depositing Conditioner, Record Id: 5656479; Mintel GNDP; May 2018; pp. 1-3.
Search Report and Written Opinion in EP18175857; dated Jan. 3, 2019; European Patent Office (EPO).
Conditioner, Record ID 3951211; Mintel GNDP; Apr. 2016; pp. 1-3.
Intense repairing conditioner, Record ID 5704005; Mintel GNDP; May 2018; pp. 1-3.
Step-3 Conditioner, Record ID 4609117; Mintel GNPD; Feb. 2017; pp. 1-4.
Search Report and Written Opinion in PCTEP2019062962; dated Aug. 2, 2019; World Intellectual Property Org. (WIPO).

PRESERVATION COMPOSITIONS

CROSS-REFERENCE TO RELATED APPLICATIONS

This application is a U.S. National Stage Application under 35 U.S.C. § 371 of International Application No. PCT/EP2019/062962, filed on May 20, 2019, which claims the benefit of European Patent Application No. 18175856.6, filed Jun. 4, 2018, the entire disclosures of which are hereby incorporated by reference for any and all purposes.

The present invention relates to preservation systems for use in consumer products.

BACKGROUND

The consumer goods industry has a constant need for agents having antimicrobial properties, in particular for the preservation of products which are otherwise perishable (such as e.g. cosmetics, pharmaceutical products or foodstuffs).

A large number of antimicrobial active compounds are already employed as preservation chemicals, but alternatives that avoid possible ecological concerns and are readily tolerated by the skin are required.

Such preservation systems should be stable, largely and preferably completely odourless, inexpensive to prepare, easy to formulate (i.e. preferably liquid) and should not be detrimental to the final product.

The present invention provides a particularly effective preservation system.

DESCRIPTION OF THE INVENTION

The present invention relates to an antimicrobial preservation system comprising:
  i. itaconic acid or salt thereof; and
  ii. a secondary preservation chemical selected from the list consisting of terpineol, geraniol, perillyl alcohol, menthol, terpinene, linalool, citronellol and mixtures thereof.

A second aspect of the invention relates to a composition comprising the antimicrobial preserving system described above.

A third aspect of the invention relates to a method of preserving a composition comprising the step of adding to the composition an antimicrobial preservation system comprising:
  i) itaconic acid or salt thereof; and
  ii) a secondary preservation chemical selected from the list consisting of terpineol, geraniol, perillyl alcohol, menthol, terpinene, linalool, citronellol and mixtures thereof.

In one embodiment of method of the invention, compound i) and ii) are pre-mixed before addition to the composition to be preserved.

In a second embodiment of method of the invention, compound i) and ii) are not pre-mixed before addition to the composition to be preserved.

DETAILED DESCRIPTION OF THE INVENTION

The present invention relates to an antimicrobial preservation system comprising itaconic acid or salt thereof, preferably the acid.

The preservation system further comprises a secondary preservation chemical selected from the list consisting of terpineol, geraniol, perillyl alcohol, menthol, terpinene, linalool, citronellol.

Preferably the secondary preservation chemical is selected from the list consisting of terpineol, geraniol, perillyl alcohol, more preferably the secondary preservation chemical is terpineol.

It is preferred if the weight ratio of compound (C1 to C6), unsaturated, organic acid having at least two carboxyl groups, preferably itaconic acid i) to secondary preservation chemical ii) is from 1:50 to 50:1 more preferably from 1:10 to 10:1, most preferably from 1:5 to 5:1.

In a preferred embodiment of the invention the preserving system is included as part of a composition. Preferably the composition is a personal care composition and more preferably the composition is a hair treatment composition.

Preferably the total the level of preserving system within the composition is from 0.05 to 5 wt % of the total composition, more preferably from 0.2% to 2 wt % of the total composition.

The compositions of the invention, comprising the preserving system of the invention, preferably comprise at least 75 wt %, preferably at least 80 wt %, more preferably at least 85 wt % and most preferably at least 87 wt % of water, by weight of the total composition.

It is preferred if the composition further comprises cationic, anionic, nonionic, zwitterionic or amphoteric surfactants or mixtures thereof.

Examples of suitable cationic surfactants which are useful include quaternary ammonium cationic surfactants corresponding to the following general formula:

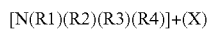

in which R1, R2, R3, and R4 are each independently selected from (a) an aliphatic group of from 1 to 22 carbon atoms, or
(b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such preferred quaternary ammonium cationic surfactants are cetyltrimethylammonium chloride (CTAC), behentrimonium chloride (BTAC) and mixtures thereof.

Alternatively, primary, secondary or tertiary fatty amines may be used in combination with an acid to provide a cationic surfactant suitable for use in the invention. The acid protonates the amine and forms an amine salt in situ. The amine is therefore effectively a non-permanent quaternary ammonium or pseudo-quaternary ammonium cationic surfactant.

Suitable fatty amines of this type include amidoamines of the following general formula:

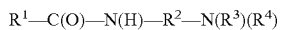

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms. Particularly preferred is stearamidopropyldimethylamine.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic (C8-C18) primary or secondary linear or branched chain alcohols or phenols with alkylene oxides, usually ethylene oxide and generally having from 6 to 30 ethylene oxide groups. Other suitable nonionics include mono- or di-alkyl alkanolamides, glycolipids preferably selected from the group of rhamnolipids and sophorolipids.

Examples include coco mono- or di-ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

Generally, the surfactants are present in shampoo compositions of the invention in an amount of from 0.1 to 50%, preferably from 5 to 30%, more preferably from 8% to 20% by weight.

The invention will now be illustrated by the following non-limiting Examples

EXAMPLES

The differing behaviours of inhibitory antimicrobials in isolation and mixtures have been widely explored using the concept of the Fractional Concentration and Fractional Inhibitory Concentration (FIC). See for instance J R W Lambert and R Lambert, J. Appl. Microbiol 95, 734 (2003); T. Jadavji, C G Prober and R Cheung, Antimicrobial Agents and Chemotherapy 26, 91 (1984), and WO 2004/006876. These parameters can be defined as follows:

FC(component $a$)=Concentration of component $a$ tested in the mixture/MIC(component $a$ tested as a single active)

FIC(component $a$)=MIC(component a tested in the mixture)/MIC(component $a$ tested as a single active)

The interactions between antimicrobials can be additive, synergistic or possibly antagonistic depending on whether the efficacy of the combination is equivalent to, greater than or less than that obtained for the same total concentration of the individual components when tested alone.

These relationships can be expressed mathematically by summing the fractional MIC values for all the components present in the mixture to give the "fractional inhibitory index":

$$\Sigma FIC = FIC_{(component\ 1)} + FIC_{(component\ 2)}$$

Such that:
$\Sigma FIC \geq 1$ corresponds to additive or antagonistic activity
$\Sigma FIC < 1$ corresponds to synergistic activity A comparable method is the calculation of the synergy index (SI) which is an industrial accepted method described by Kull, F. C.; Eisman, P. C.; Sylwestrowicz, H. D. and Mayer, R. L., in Applied Microbiology 9:538-541 (1961).

Methods

Liquid broth assays (MIC and checkerboard) were conducted to identify the minimum concentration(s) of individual and binary combinations of preservation chemicals. A modified methodology to ISO 20776-1:2006 was utilised for the screening as follows. Stock solutions of preservation chemicals and tryptic soy broth were inoculated with 1-5× $10^6$ microorganisms and incubated at 30° C. for 24 hours, after which optical densities at $OD_{600}$ nm were measured. MIC was defined as the concentration at which <25% growth was observed in comparison to a positive growth control containing no preservation chemicals. Preservation chemicals were screened at a concentration range of 0.0156-2%.

TABLE 1

Microorganism pools
Microorganism pool

| Pool 1 | Gram negative non-fermenting bacteria: Pseudomonas aeruginosa, Pseudomonas putida & Burkholderia cepacia |
| Pool 2 | Gram negative fermenting bacteria: Enterobacter gergoviae & Klebsiella species |

TABLE 2

Chemical combination synergy scores

| | ΣFIC synergy score | | | |
| | Itaconic acid | | Citric Acid | |
| | Pool 1 | Pool 2 | Pool 1 | Pool 2 |
| Terpeniol | 0.5 | 0.38 | 1 | 0.75 |
| Geraniol | 0.31 | 0.5 | 0.75 | 1.06 |
| Perillyl alcohol | 0.38 | 0.38 | 0.38 | 0.5 |

The invention claimed is:
1. An antimicrobial preservation system comprising: i) itaconic acid or salt thereof and ii) a secondary preservation chemical comprising perillyl alcohol.

2. The preservation system according to claim 1 wherein the secondary preservation chemical further comprises an additional preservation chemical selected from the group consisting of terpineol, geraniol, menthol, terpinene, linalool, citronellol and mixtures thereof.

3. The preservation system according to claim 1, wherein the secondary preservation chemical further comprises the additional preservation chemical terpineol.

4. The preservation system according to claim 1, wherein the weight ratio of compound i) to compound ii) is from 1:50 to 50:1.

5. The preservation system according to claim 1, wherein the weight ratio of compound i) to compound ii) is from 1:10 to 10:1.

6. An aqueous composition comprising the preservation system according to claim 1.

7. The composition according to claim 6 comprising at least 75 wt % water, by weight of the total composition.

8. The composition according to claim 6, wherein the preserving system comprises from 0.05 to 5 wt % of the total composition.

9. The composition according to claim 6 which is a personal care composition.

10. The composition according to claim 9 which is a hair treatment composition.

11. A method of preserving a composition comprising the step of adding to the composition an antimicrobial preservation system comprising: i) itaconic acid or salt thereof and ii) a secondary preservation chemical comprising perillyl alcohol.

12. The method according to claim 11, wherein compounds i) and ii) are pre-mixed before addition to the composition to be preserved.

13. The method according to claim 11, wherein compounds i) and ii) are not pre-mixed before addition to the composition to be preserved.

* * * * *